United States Patent [19]

Matsuyama et al.

[11] 4,255,244
[45] Mar. 10, 1981

[54] SHRINK TUBE LIQUID JUNCTION STRUCTURE FOR ELECTROCHEMICAL ELECTRODES

[75] Inventors: George Matsuyama; Grover F. Lindell, both of Santa Ana, Calif.

[73] Assignee: Beckman Instruments, Inc., Fullerton, Calif.

[21] Appl. No.: 55,253

[22] Filed: Jul. 6, 1979

[51] Int. Cl.³ ............................................. G01N 27/30
[52] U.S. Cl. ............................ 204/195 F; 204/195 R; 204/195 G; 204/195 M
[58] Field of Search ........... 204/195 F, 195 G, 195 R, 204/195 M; 324/438

[56] References Cited

U.S. PATENT DOCUMENTS

| | | | |
|---|---|---|---|
| 3,575,834 | 4/1971 | Hoole et al. | 204/195 F |
| 3,718,569 | 2/1973 | Petersen et al. | 204/195 G |
| 3,880,737 | 4/1975 | Brunt | 204/195 G |
| 4,012,308 | 3/1977 | Jerrold-Jones et al. | 204/195 F |
| 4,116,798 | 9/1978 | Magar et al. | 204/195 F |

Primary Examiner—G. L. Kaplan
Attorney, Agent, or Firm—R. J. Steinmeyer; Robert R. Meads; John R. Shewmaker

[57] ABSTRACT

A liquid junction structure for an electrochemical reference electrode or a reference portion of an electrochemical combination electrode comprising an element of capillary material restrained between first and second plastic shrink tubes.

8 Claims, 4 Drawing Figures

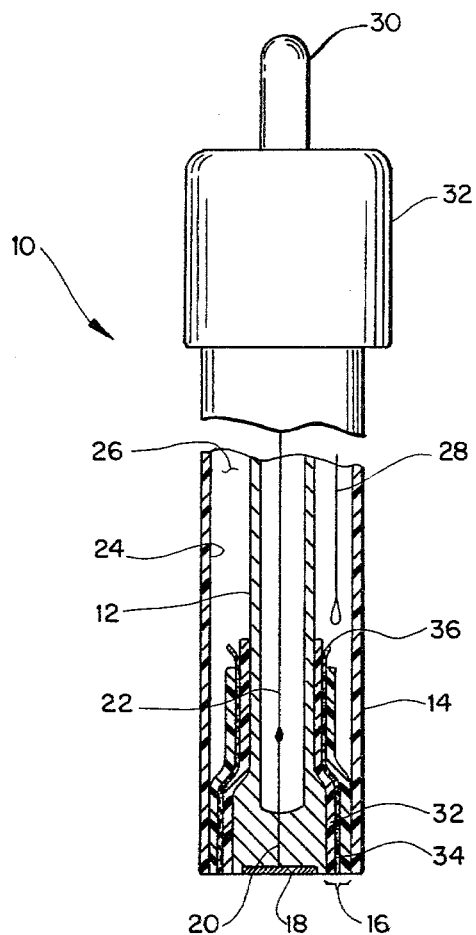
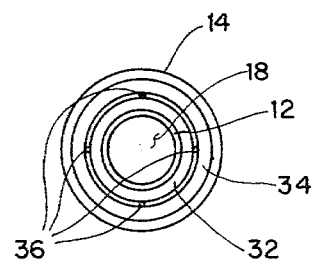
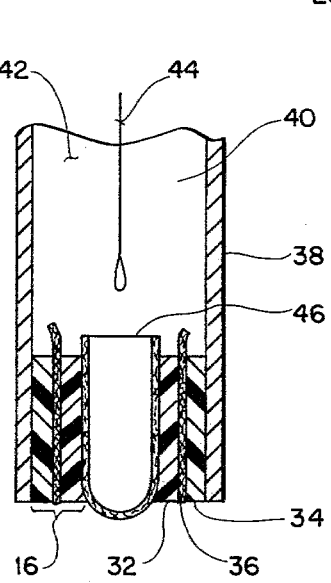
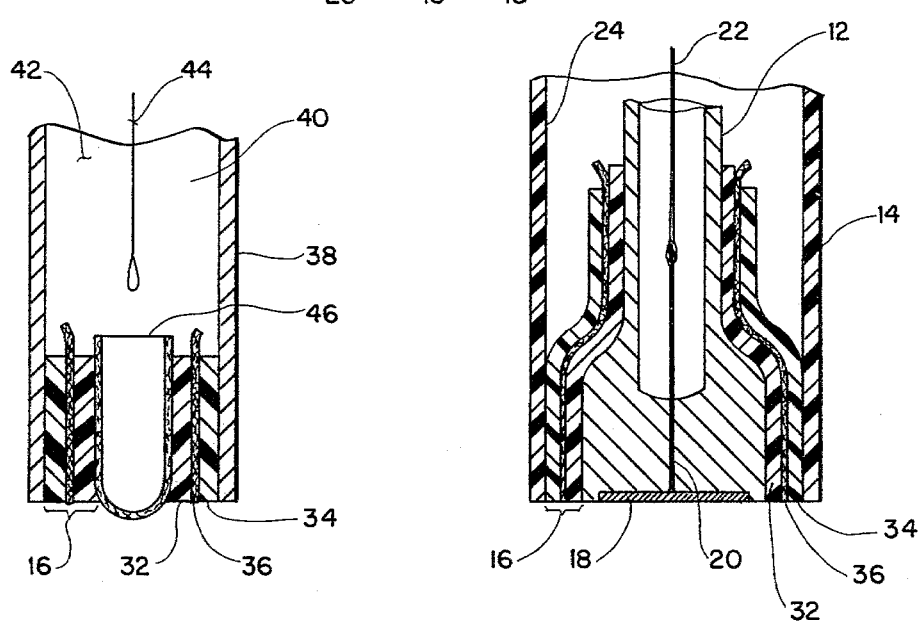
FIG. 1
FIG. 2
FIG. 4
FIG. 3

SHRINK TUBE LIQUID JUNCTION STRUCTURE FOR ELECTROCHEMICAL ELECTRODES

BACKGROUND OF THE INVENTION

1. Field of the Invention

The present invention relates generally to liquid junction structures for electrochemical electrodes and, more particularly, to shrink tube liquid junction structures useful in electrochemical combination and reference electrodes.

2. Description of the Prior Art

Electrochemical ion measurements are typically made by contacting a test solution with a measuring electrode and a reference electrode and measuring the potential difference between the two electrodes. The measuring electrode is typically a high impedance device for measuring activity or concentration of the ion in question and accordingly generates a potential with respect to the test solution related to the concentration of the ion of interest. The reference electrode provides a potential that is substantially independent of the test solution composition. Typically, the reference electrode comprises a metal conductor in contact with a mass of sparingly soluble salt of the metal and immersed in an electrolyte having a nonmetallic ion in common with the metal salt. Such reference electrodes often employ a silver wire conductor coated at one end with silver chloride and immersed in a potassium chloride electrolyte solution contained within the electrode.

It is now commonplace for a reference electrode and a measuring electrode to be combined in a single structure referred to as a combination electrode having an ion measuring portion and a reference portion. In a typical form a combination electrode comprises an inner generally tubular electrode body having an ion measuring structure at one end, a generally tubular container surrounding and receiving the inner electrode body, and a reference electrolyte reservoir defined in the annular space between the body and container.

To make ion measurements, it is necessary for the reference electrolyte, within a reference electrode or within the reference portion of a combination electrode, to electrolytically contact the test solution to be measured. For this purpose numerous so-called liquid junction structures have been developed to establish an electrolytic path between the electrolyte and the test solution. Typically such is accomplished by means of a wettable capillary material which provides either a minute flow rate path or an ion diffusion path between the electrolyte and the test solution. An early but still popular liquid junction structure employs one or more strands of capillary fibers, such as asbestos or linen, in contact with the reference electrolyte and with the test solution. U.S. Pat. No. 4,012,308 illustrates one such liquid junction comprising a plurality of asbestos fiber strands around and extending through an annular seal between an inner glass pH electrode body and an outer tubular plastic container. The strands are looped through an elastomeric band which surrounds the glass electrode body and holds the strands in place against the glass body.

In another fiber strand liquid junction a plastic shrink tube positioned about and shrunk onto the inner glass pH electrode body traps and restrains the asbestos fiber strands in place against the glass electrode body.

While satisfactory electrodes result with the two foregoing liquid junction structure arrangements, their operation is compromised by the existence of undesirable stirring artifacts and liquid junction potentials. Such result because an ideal liquid junction structure through the asbestos fibers alone is not attained in actual practice. It is believed that since the asbestos strands are restrained by the shrink tubing against the relatively hard outer surface of the inner glass electrode body, voids or pockets remain along the length of the fiber material adjacent the hard glass body in which secondary parallel paths bypassing the fiber material develop between the reference electrolyte and the solution to be tested. Such result in the aforementioned stirring artifacts and liquid junction potentials which reduce the accuracy and reliability of the electrode.

SUMMARY OF THE INVENTION

The present invention resides in a new and improved shrink tube liquid junction structure for electrochemical electrodes which overcomes the disadvantages of the prior arrangements. The liquid junction structure is simple in construction and reliable in operation and is particularly adapted for though not limited to use with capillary material in the form of fiber strands.

To the foregoing ends the present invention in its broadest aspects resides in a liquid junction structure in which an element of capillary material is restrained between a first and a second shrink tube and as thus restrained extends from a point contacting electrolyte of the associated electrochemical electrode to a point for contacting the solution to be tested. In one embodiment the liquid junction structure is part of a combination electrode comprising an elongated ion measuring electrode body received within a hollow container surrounding the electrode body defining an electrolyte reservoir in a space therebetween. A first plastic shrink tube is positioned about and shrunk around the electrode body and a second plastic shrink tube is positioned about and shrunk around the first shrink tube with the element of capillary material restrained between the first and second shrink tubes. In a second embodiment defining a reference electrode the shrink tubes are shrunk around an inner tubular or solid body received in and surrounded by the hollow container.

Restraining the capillary material element between the two plastic shrink tubes allows the tubes to form or mold completely around the capillary material without forming voids or pockets adjacent and therealong. Accordingly, electrodes incorporating such a liquid junction structure are less susceptible to stirring artifacts and liquid junction potentials.

BRIEF DESCRIPTION OF THE DRAWING

FIG. 1 is a partial side elevational and partial cross-sectional view of a combination electrode incorporating the liquid junction structure of the present invention. The electrode is broken along its length with the upper end depicted in side elevation and the lower end illustrated in cross-section in a generally vertical plane.

FIG. 2 is a bottom plan view of the electrode of FIG. 1.

FIG. 3 is an enlarged fragmentary sectional view of the lower end of the FIG. 1 electrode.

FIG. 4 is a fragmentary cross-sectional view taken in a generally vertical plane through the lower end of a reference electrode incorporating the present invention.

DESCRIPTION OF THE PREFERRED EMBODIMENTS

As shown in the drawing for purposes of illustration, and particularly FIGS. 1-3 thereof, the invention is there embodied in an electrochemical combination electrode 10 comprising a measuring electrode body 12 supported near its opposite ends to extend coaxially within a generally tubular hollow container 14 and between which is defined a novel shrink tube liquid junction structure 16 in accordance with the present invention. Container 14 is formed of a durable nonconductive material such as polyethylene, polypropylene, or a fluorocarbon plastic. Measuring electrode 12 comprises a generally tubular glass body having a somewhat enlarged solid lower end within the lower face of which is supported an ion measuring structure 18. The illustrated electrode is a combination platinum electrode and accordingly structure 18 comprises a platinum disc supported by body 12 with the exposed face of the disc disposed for contacting a test solution. Electrical connection to the platinum disc is provided by a platinum wire 20 welded thereto and extending upwardly therefrom through body 12 toward the upper end of the electrode. If desired, the length of the platinum wire may be kept relatively short to reduce costs and a copper wire 22 welded thereto may provide the major length of the axially extending wire electrode within body 12.

An annular reference electrolyte reservoir 24 is defined between the exterior of glass electrode body 12 and the interior of hollow container 14. The reservoir 24 contains a suitable reference electrolyte such as saturated KCl solution with or without a gelling agent and with or without solid KCl crystals or other electrolytes depending on the type of reference electrode desired. A reference half cell 28 comprising a silver wire conductor coated at its lower end with silver chloride extends axially into reservoir 24 immersed in electrolyte 26.

At the upper end of the combination electrode a connecting coaxial cable 30 is connected to wire electrode 22 and half cell 28 and the electrode is closed by a cap 32 all in a conventional manner.

Proper operation of electrode 10 requires that half cell 28 be in stable electrolytic contact with a test solution containing the ions to be detected to enable the reference half cell to establish a stable potential. This is accomplished by direct contact of reference electrolyte 24 with a test solution through the liquid junction structure 16. In accordance with a primary aspect of the present invention, the liquid junction structure comprises a first plastic shrink tube 32 positioned about and shrunk around the lower end of glass electrode body 12 and a second plastic shrink tube 34 positioned about and shrunk around the first tube. One or more elements of wettable capillary material 36 are restrained between the two shrink tubes 32 and 34 and extend from a point in the lower end of the electrode exposed to the test solution to a point within reference electrolyte reservoir 24 exposed to the electrolyte 26. The elements of capillary material may take the form of strands of quartz fibers, linen threads, woven Dacron line, or the like. The precise structure and composition of the capillary material, whether it is a straight strand or a mesh-like material, or the like is not critical as long as one or more electrolytic paths are established through the material connecting the reference electrolyte and the test solution. For the illustrated platinum combination electrode, FIG. 2 illustrates two such capillary material elements 36 exposed at two diametrically opposed points at the end of the measuring electrode body 12. What is important is that the capillary elements of however many in number are restrained between the shrink tubes 32 and 34 allowing complete molding of the tubes around the elements.

Shrink tubes 32 and 34 are suitably formed of a silicone rubber material which is available from Raychem Corporation and which is described in a publication titled "SFR Elastomer Tubing" of such company dated June 1977. The liquid junction structure 16 of the invention is manufactured after securing the platinum disc 18 and wires 20 and 22 to the electrode body 12. Thereafter a first sleeve 32 of the shrink tube material about 0.9 inches in length is slipped over the lower end of electrode 12 and heated to about 400° C. to cause the sleeve to shrink and contract tightly around the electrode body. Thereafter one or more strands 36 of asbestos or other suitable capillary material elements are laid evenly on and around the outer surface of shrink tube sleeve 32 and are temporarily held in place thereon by masking tape. A second sleeve 34 of the shrink tube material about 0.8 inches in length is slipped over and around sleeve 32 and the capillary elements held thereon to a point slightly below the top of sleeve 32. Sleeve 34 is then heated to cause the sleeve 34 to shrink and contract tightly around sleeve 32 and the capillary elements. Significantly, heating causes the two shrink tubes to mold and form completely around the length of the capillary elements compacting thereabout and restraining the elements in place without forming voids or pockets adjacent and along the elements. The length of the restrained capillary elements is such that the ends protrude slightly from between the shrink tubes at both the lower and upper ends thereof.

With the liquid junction structure 16 in place around glass electrode body 12, the hollow container 14 is pressed over electrode 12 and liquid junction structure 16 to align the lower end of container 14 flush with the bottom face of platinum disc 18 defining a planar sensing end for the electrode 10. The inner circumference of tube 14 is sealed to the outer circumference of shrink tube 34. Thereafter the shrink tubing and capillary elements are trimmed with a knife flush with the same bottom face. This therefore completes the planar sensing bottom end for the combination electrode.

While the invention has been embodied above in a platinum ion measuring electrode, it should be emphasized that its use extends to the measurement of any other ions and that other types of ion measuring structures or membrane 18 would be employed for other ions of interest. Consequently the type of measuring electrode 12, the particular ion sensing structure 18 and the appropriate connection thereto will vary widely. For example, electrode 12 could be a conventional pH sensing electrode having a hydrogen sensitive glass membrane at its lower end.

Referring now to FIG. 4, there is shown a preferred embodiment of a reference electrode incorporating the liquid junction structure 16 of the present invention. The figure depicts the lower end of an electrode comprising a generally tubular container 38 the interior of which defines a reference electrolyte reservoir 40 containing reference electrolyte 42 in which is immersed a reference half cell 44. The liquid junction structure is supported at the lower end of container 38 by an inner body 46 of a nonconductive material such as glass or plastic having a generally cylindrical or tubular construction illustrated in the figure or which may be a solid rod, if desired. What is important is that the inner body simply be of a configuration around which plastic shrink tubes 32 and 34 may be positioned and shrunk to restrain the strands of capillary material 36 therebetween in a position establishing the electrolytic paths between reference electrolyte 42 and the test solution in which the reference electrode is immersed.

From the foregoing it will be apparent that the invention provides an improved liquid junction structure for either reference or combination electrodes exhibiting important advantages in manufacture and operation over electrodes which existed heretofore.

The fabrication of the electrode is greatly simplified and the junctions produced have uniform, good-performance characteristics. Since the plastic tubes are elastomeric they can be formed on tapered or irregularly shaped electrode bodies such as the enlarged tapered lower end of electrode body 12 (FIG. 3). The elastomeric tubes contain the capillary material in a uniform, well-sealed configuration. The elastomeric tubes also seal tightly to the inner tube and outer body so the electrolyte path is solely through the capillary material. Moreover, while several preferred embodiments of the invention have been illustrated and described, it will be apparent that modifications may be made therein without departing from the spirit and scope of the invention as defined in the appended claims.

What is claimed is:

1. In a combination electrode comprising an elongated electrode body having an ion measuring structure at an end thereof for contacting a test solution and a hollow container receiving and surrounding the electrode body defining an electrolyte reservoir in a space therebetween, an improved liquid junction structure for establishing electrolytic communication between electrolyte in the reservoir and the test solution comprising:

a first plastic shrink tube positioned about and shrunk around the electrode body;

a second plastic shrink tube positioned about and shrunk around the first shrink tube; and an element of capillary material restrained between the first and second shrink tubes and extending therethrough from a point contacting the electrolyte to a point for contacting the test solution.

2. The electrode of claim 1 wherein the element of capillary material comprises one or more strands of material around which the first and second shrink tubes compact and mold in a manner precluding formation of voids or pockets around the strand whereby a liquid junction path is established between the electrolyte and the test solution solely through the capillary material.

3. The electrode of claim 1 or claim 2 wherein the hollow container is generally tubular in shape and wherein the electrode body and the first and second shrink tubes shrunk therearound are received and supported coaxially within an open end of the hollow container.

4. The electrode of claim 3 wherein:

the first and second shrink tubes are disposed at the end of the elongated electrode proximate the ion measuring structure; and the ion measuring structure and an exposed portion of the capillary element for contacting the solution are generally co-planar at the end of the combination electrode.

5. In a reference electrode comprising a hollow container and an electrolyte reservoir therein, an improved liquid junction structure closing an opening in the hollow container for establishing electrolyte communication between electrolyte and the reservoir and the test solution comprising:

an inner body in the container opening;

a first plastic shrink tube positioned about and shrunk around the inner body;

a second plastic shrink tube positioned about and shrunk around the first shrink tube; and an element of capillary material restrained between the first and second shrink tubes and extending therethrough from a point contacting the electrolyte to a point for contacting the test solution.

6. In an electrochemical electrode comprising a hollow container and an electrolyte reservoir therein, an improved liquid junction structure closing an opening in the hollow container for establishing electrolytic communication between electrolyte in the reservoir and a test solution comprising:

an element of capillary material restrained between first and second plastic shrink tubes and as thus restrained extending therethrough from a point contacting the electrolyte to a point for contacting the test solution.

7. The electrode of claim 6 wherein the tubes mold and compact around the capillary element in a manner precluding formation of voids or pockets around the element whereby a liquid junction path is established between the electrolyte and the test solution solely through the capillary material.

8. The electrode of claim 7 wherein the tubes are supported in a shrink fit on and surrounding an inner body disposed in an opening of the hollow container.

* * * * *